US012564396B2

(12) United States Patent
Richards

(10) Patent No.: US 12,564,396 B2
(45) Date of Patent: Mar. 3, 2026

(54) SUTURE BASED CLOSURE DEVICE

(71) Applicant: Boston Scientific Scimed, Inc., Maple Grove, MN (US)

(72) Inventor: Laura Emily Richards, Plainville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 46 days.

(21) Appl. No.: 18/524,849

(22) Filed: Nov. 30, 2023

(65) Prior Publication Data

US 2024/0180547 A1 Jun. 6, 2024

Related U.S. Application Data

(60) Provisional application No. 63/429,399, filed on Dec. 1, 2022.

(51) Int. Cl.
A61B 17/04 (2006.01)
A61B 17/00 (2006.01)

(52) U.S. Cl.
CPC .................... A61B 17/0469 (2013.01); *A61B 2017/00398* (2013.01)

(58) Field of Classification Search
CPC .................. A61B 17/0469; A61B 2017/00398
See application file for complete search history.

(56) References Cited

U.S. PATENT DOCUMENTS

| | | |
|---|---|---|
| 5,478,344 A | 12/1995 | Stone |
| 5,584,861 A | 12/1996 | Swain et al. |

| | | |
|---|---|---|
| 5,766,186 A | 6/1998 | Faraz et al. |
| 6,086,608 A | 7/2000 | Ek et al. |
| 6,200,329 B1 | 3/2001 | Fung et al. |
| 6,494,888 B1 | 12/2002 | Laufer et al. |
| 6,506,196 B1 | 1/2003 | Laufer |

(Continued)

FOREIGN PATENT DOCUMENTS

| | | |
|---|---|---|
| CA | 2682488 A1 | 10/2008 |
| DE | 202005022017 U1 | 5/2012 |

(Continued)

OTHER PUBLICATIONS

Invitation to Pay Additional Fees dated Apr. 18, 2024 for International Application No. PCT/US2023/081844.

(Continued)

*Primary Examiner* — Phong Son H Dang
(74) *Attorney, Agent, or Firm* — Seager, Tufte & Wickhem, LLP

(57) ABSTRACT

A suture device includes a suturing body defining a circular track that extends around a periphery of the suturing body, the circular track including an open portion adapted to allow tissue to enter the open portion. A curved shuttle is disposed within the circular track, the curved shuttle including a pointed leading edge and adapted to hold a suture relative to the curved shuttle. In some cases, a curved pusher is disposed within the circular track and is adapted to push the curved shuttle around the circular track in a first direction around the circular track such that the pointed leading edge penetrates any tissue disposed within the open portion. In some cases, electromagnets may be used to move the curved shuttle relative to the suturing body.

18 Claims, 8 Drawing Sheets

(56) References Cited

U.S. PATENT DOCUMENTS

| | | | |
|---|---|---|---|
| 6,554,845 B1 | 4/2003 | Fleenor et al. | |
| 6,569,085 B2 | 5/2003 | Kortenbach et al. | |
| 6,626,917 B1 | 9/2003 | Craig | |
| 6,663,639 B1 | 12/2003 | Laufer et al. | |
| 6,719,763 B2 | 4/2004 | Chung et al. | |
| 6,740,030 B2 | 5/2004 | Martone et al. | |
| 6,746,457 B2 | 6/2004 | Dana et al. | |
| 6,755,843 B2 | 6/2004 | Chung et al. | |
| 6,773,441 B1 | 8/2004 | Laufer et al. | |
| 6,808,491 B2 | 10/2004 | Kortenbach et al. | |
| 6,821,285 B2 | 11/2004 | Laufer et al. | |
| 6,835,200 B2 | 12/2004 | Laufer et al. | |
| 6,908,427 B2 | 6/2005 | Fleener et al. | |
| 6,997,931 B2 | 2/2006 | Sauer et al. | |
| 7,056,284 B2 | 6/2006 | Martone et al. | |
| 7,063,710 B2 | 6/2006 | Takamoto et al. | |
| 7,063,715 B2 | 6/2006 | Onuki et al. | |
| 7,094,246 B2 | 8/2006 | Anderson et al. | |
| 7,144,401 B2 | 12/2006 | Yamamoto et al. | |
| 7,147,646 B2 | 12/2006 | Dana et al. | |
| 7,153,314 B2 | 12/2006 | Laufer et al. | |
| 7,220,266 B2 | 5/2007 | Gambale | |
| 7,232,445 B2 | 6/2007 | Kortenbach et al. | |
| 7,235,086 B2 | 6/2007 | Sauer et al. | |
| 7,326,221 B2 | 2/2008 | Sakamoto et al. | |
| 7,344,545 B2 | 3/2008 | Takemoto et al. | |
| 7,347,863 B2 | 3/2008 | Rothe et al. | |
| 7,361,180 B2 | 4/2008 | Saadat et al. | |
| 7,530,985 B2 | 5/2009 | Takemoto et al. | |
| 7,601,161 B1 | 10/2009 | Nobles et al. | |
| 7,618,425 B2 | 11/2009 | Yamamoto et al. | |
| 7,713,277 B2 | 5/2010 | Laufer et al. | |
| 7,722,633 B2 | 5/2010 | Laufer et al. | |
| 7,727,246 B2 | 6/2010 | Sixto, Jr. et al. | |
| 7,736,373 B2 | 6/2010 | Laufer et al. | |
| 7,776,057 B2 | 8/2010 | Laufer et al. | |
| 7,776,066 B2 | 8/2010 | Onuki et al. | |
| 7,842,051 B2 | 11/2010 | Dana et al. | |
| 7,846,180 B2 | 12/2010 | Cerier | |
| 7,857,823 B2 | 12/2010 | Laufer et al. | |
| 7,896,893 B2 | 3/2011 | Laufer et al. | |
| 7,918,867 B2 | 4/2011 | Dana et al. | |
| 7,951,157 B2 | 5/2011 | Gambale | |
| 7,992,571 B2 | 8/2011 | Gross et al. | |
| 7,993,368 B2 | 8/2011 | Gambale et al. | |
| 8,016,840 B2 | 9/2011 | Takemoto et al. | |
| 8,021,376 B2 | 9/2011 | Takemoto et al. | |
| 8,057,494 B2 | 11/2011 | Laufer et al. | |
| 8,062,314 B2 | 11/2011 | Sixto, Jr. et al. | |
| 8,066,721 B2 | 11/2011 | Kortenbach et al. | |
| 8,105,355 B2 | 1/2012 | Page et al. | |
| 8,211,123 B2 | 7/2012 | Gross et al. | |
| 8,216,253 B2 | 7/2012 | Saadat et al. | |
| 8,226,667 B2 | 7/2012 | Viola et al. | |
| 8,277,468 B2 | 10/2012 | Laufer et al. | |
| 8,287,554 B2 | 10/2012 | Cerier et al. | |
| 8,287,556 B2 | 10/2012 | Gilkey et al. | |
| 8,308,765 B2 | 11/2012 | Saadat et al. | |
| 8,313,496 B2 | 11/2012 | Sauer et al. | |
| 8,361,089 B2 | 1/2013 | Chu | |
| 8,388,632 B2 | 3/2013 | Gambale | |
| 8,425,555 B2 | 4/2013 | Page et al. | |
| 8,454,631 B2 | 6/2013 | Viola et al. | |
| 8,465,506 B2 | 6/2013 | McLawhorn et al. | |
| 8,480,691 B2 | 7/2013 | Dana et al. | |
| 8,500,756 B2 | 8/2013 | Papa et al. | |
| 8,540,735 B2 | 9/2013 | Mitelberg et al. | |
| 8,551,120 B2 | 10/2013 | Gambale | |
| 8,585,720 B2 | 11/2013 | Gross et al. | |
| 8,632,553 B2 | 1/2014 | Sakamoto et al. | |
| 8,641,728 B2 | 2/2014 | Stokes et al. | |
| 8,679,136 B2 | 3/2014 | Mitelberg | |
| 8,709,022 B2 | 4/2014 | Stone et al. | |
| 8,764,771 B2 | 7/2014 | Chu | |
| 8,882,785 B2 | 11/2014 | DiCesare et al. | |
| 8,926,634 B2 | 1/2015 | Rothe et al. | |
| 8,992,570 B2 | 3/2015 | Gambale et al. | |
| 9,011,466 B2 | 4/2015 | Adams et al. | |
| 9,072,480 B2 | 7/2015 | Hart et al. | |
| 9,089,325 B2 | 7/2015 | Mitelberg et al. | |
| 9,125,646 B2 | 9/2015 | Woodard, Jr. et al. | |
| 9,198,562 B2 | 12/2015 | Mitelberg et al. | |
| 9,320,515 B2 | 4/2016 | Dana et al. | |
| 9,445,807 B2 * | 9/2016 | Brecher | A61B 17/06066 |
| 9,486,126 B2 | 11/2016 | West et al. | |
| 9,498,207 B2 | 11/2016 | Martin et al. | |
| 9,504,465 B2 | 11/2016 | Chu | |
| 9,510,817 B2 | 12/2016 | Saadat et al. | |
| 9,549,728 B2 | 1/2017 | Chu | |
| 9,675,339 B2 * | 6/2017 | Brecher | A61B 17/0482 |
| 9,750,494 B2 | 9/2017 | Gross et al. | |
| 9,788,830 B2 * | 10/2017 | Martin | A61B 17/0482 |
| 9,788,831 B2 | 10/2017 | Mitelberg | |
| 9,833,232 B2 | 12/2017 | Woodard, Jr. et al. | |
| 9,844,366 B2 | 12/2017 | Woodard, Jr. et al. | |
| 9,867,610 B2 | 1/2018 | Mitelberg et al. | |
| 10,045,871 B2 | 8/2018 | Saadat et al. | |
| 10,143,463 B2 | 12/2018 | Dana et al. | |
| 10,194,902 B2 | 2/2019 | Nobles et al. | |
| 10,292,698 B2 * | 5/2019 | Meade | A61B 17/0625 |
| 10,335,142 B2 | 7/2019 | Raybin et al. | |
| 10,736,625 B1 | 8/2020 | Penn, IV et al. | |
| 11,253,250 B2 * | 2/2022 | Meade | A61B 17/0482 |
| 2002/0107530 A1 | 8/2002 | Sauer et al. | |
| 2003/0181924 A1 | 9/2003 | Yamamoto et al. | |
| 2003/0195529 A1 | 10/2003 | Takamoto et al. | |
| 2003/0204205 A1 | 10/2003 | Sauer et al. | |
| 2004/0002699 A1 | 1/2004 | Ryan et al. | |
| 2004/0138706 A1 | 7/2004 | Abrams et al. | |
| 2005/0033319 A1 | 2/2005 | Gambale et al. | |
| 2005/0250985 A1 | 11/2005 | Saadat et al. | |
| 2006/0030868 A1 | 2/2006 | Bennett, III | |
| 2006/0111732 A1 | 5/2006 | Gibbons et al. | |
| 2006/0282094 A1 | 12/2006 | Stokes et al. | |
| 2007/0270908 A1 | 11/2007 | Stokes et al. | |
| 2008/0086148 A1 | 4/2008 | Baker et al. | |
| 2009/0177031 A1 | 7/2009 | Surti et al. | |
| 2010/0016870 A1 | 1/2010 | Campbell | |
| 2010/0137681 A1 | 6/2010 | Ewers et al. | |
| 2010/0198006 A1 | 8/2010 | Greenburg et al. | |
| 2011/0152891 A1 | 6/2011 | McLawhorn et al. | |
| 2011/0276064 A1 | 11/2011 | Henrichsen et al. | |
| 2012/0158023 A1 | 6/2012 | Miltelberg et al. | |
| 2012/0271327 A1 | 10/2012 | West et al. | |
| 2012/0277768 A1 | 11/2012 | Viola et al. | |
| 2013/0046335 A1 | 2/2013 | Deutsch et al. | |
| 2013/0096581 A1 | 4/2013 | Gilkey et al. | |
| 2013/0304093 A1 | 11/2013 | Serina et al. | |
| 2014/0121457 A1 | 5/2014 | Mort et al. | |
| 2014/0128668 A1 | 5/2014 | Cox et al. | |
| 2015/0126983 A1 | 5/2015 | Alvarado et al. | |
| 2016/0045197 A1 | 2/2016 | Mitelberg et al. | |
| 2017/0035413 A1 | 2/2017 | Takahashi | |
| 2017/0042534 A1 | 2/2017 | Nobles et al. | |
| 2017/0086817 A1 | 3/2017 | Mitelberg | |
| 2017/0086818 A1 | 3/2017 | Mitelberg | |
| 2017/0119371 A1 | 5/2017 | Mims et al. | |
| 2017/0319197 A1 | 11/2017 | Gross et al. | |
| 2018/0042602 A1 | 2/2018 | Mitelberg et al. | |
| 2018/0042603 A1 | 2/2018 | Mitelberg et al. | |
| 2018/0153381 A1 | 6/2018 | Wei et al. | |
| 2018/0221009 A1 | 8/2018 | Mitelberg et al. | |
| 2018/0235604 A1 | 8/2018 | Comee et al. | |
| 2018/0344501 A1 | 12/2018 | Saadat et al. | |
| 2021/0298742 A1 | 9/2021 | Bagley | |
| 2022/0338866 A1 | 10/2022 | Bagley et al. | |

FOREIGN PATENT DOCUMENTS

| | | | |
|---|---|---|---|
| EP | 1354558 A2 | 10/2003 | |
| EP | 1520509 A1 | 4/2005 | |
| EP | 2108304 A2 | 10/2009 | |
| EP | 2515767 A1 | 7/2011 | |
| JP | 2003305046 A | 10/2003 | |

(56)                References Cited

FOREIGN PATENT DOCUMENTS

| JP | 2013514866 A | 5/2013 |
|----|----|----|
| WO | 0101868 A1 | 1/2001 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2010085793 A1 | 7/2010 |
| WO | 2012096280 A1 | 7/2012 |
| WO | 2013022959 A2 | 2/2013 |
| WO | 2016200811 A1 | 12/2016 |
| WO | 2017087856 A1 | 5/2017 |
| WO | 2018156603 A1 | 8/2018 |
| WO | 2021202508 A1 | 10/2021 |

OTHER PUBLICATIONS

International Search Report and Written Opinion dated Aug. 20, 2019 for International Application No. PCT/US2019/033748.

International Search Report and Written Opinion dated Oct. 1, 2019 for International Application No. PCT/US2019/038006.

Invitation to Pay Additional Fees dated Sep. 26, 2019 for International Application No. PCT/US2019/037995.

International Search Report and Written Opinion dated Dec. 6, 2019 for International Application No. PCT/US2019/037995.

Invitation to Pay Additional Fees dated Nov. 18, 2019 for International Application No. PCT/US2019/049774.

International Search Report and Written Opinion dated Sep. 20, 2019 for International Application No. PCT/US2019/039312.

International Search Report and Written Opinion dated Jun. 17, 2021 for International Application No. PCT/US2021/024855.

Korean Intellectual Property Office, Office Action, KR Application No. 10-2019-7027516, Mar. 29, 2021 (11 pgs).

International Search Report and Written Opinion dated May 22, 2018 for International Application No. PCT/US2018/018982.

International Search Report and Written Opinion dated Aug. 4, 2022 for International Application No. PCT/US2022/026369.

International Search Report and Written Opinion dated Jun. 17, 2021 for International Application No. PCT/US2022/024855.

* cited by examiner

SUTURE BASED CLOSURE DEVICE

CROSS-REFERENCE TO RELATED APPLICATIONS

This application claims the benefit of priority under 35 U.S.C. § 119 of U.S. Provisional Application No. 63/429,399, filed Dec. 1, 2022, the entire disclosure of which is hereby incorporated by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. An example may be found in a suture device that is adapted for use with a delivery system having a lumen extending therethrough. The suture device includes a suturing body adapted to be releasably secured relative to a distal end of the delivery system, the suturing body defining a circular track that extends around a periphery of the suturing body, the circular track including an open portion adapted to allow tissue to enter the open portion. A curved shuttle is disposed within the circular track, the curved shuttle including a pointed leading edge and adapted to hold a suture relative to the curved shuttle.

Alternatively or additionally, the circular track may extend within a plane, and the suturing body may extend orthogonally to the plane.

Alternatively or additionally, the suture device may further include a curved pusher disposed within the circular track and adapted to push the curved shuttle around the circular track in a first direction around the circular track such that the pointed leading edge penetrates any tissue disposed within the open portion.

Alternatively or additionally, the curved pusher may be operably coupled with an elongate member such that rotation of the elongate member causes the curved pusher to push the curved shuttle around the circular track in the first direction.

Alternatively or additionally, the elongate member may be adapted to be manually rotated relative to the suturing body.

Alternatively or additionally, the suture device may further include a motor adapted to rotate the elongate member relative to the suturing body.

Alternatively or additionally, the suture device may further include a plurality of electromagnets disposed within the suturing body and a plurality of magnets disposed within the curved shuttle, wherein actuating the electromagnets within the suturing body with an alternating polarity may cause the curved shuttle to translate within the circular track.

Alternatively or additionally, the suture may be attached to a tail piece that is temporarily held in place at a second end of the curved shuttle.

Another example may be found in a medical device that is adapted for use with a delivery system having a lumen extending therethrough. The medical device includes a suturing body adapted to be releasably secured relative to a distal end of the delivery system, the suturing body defining a circular track that extends around a periphery of the suturing body, the circular track including an open portion adapted to allow tissue to enter the open portion. A curved shuttle is disposed within the circular track, the curved shuttle including a pointed leading edge and adapted to hold a suture relative to the curved shuttle. A curved pusher is disposed within the circular track and adapted to push the curved shuttle around the circular track in a first direction around the circular track such that the pointed leading edge penetrates any tissue disposed within the open portion. An elongate member is coupled with the curved pusher such that rotation of the elongate member causes the curved pusher to push the curved shuttle around the circular track in the first direction.

Alternatively or additionally, the elongate member may extend coaxially through the suturing body.

Alternatively or additionally, the suturing body may extend orthogonally to a plane in which the circular track is disposed.

Alternatively or additionally, the elongate member may be adapted to be manually rotated relative to the suturing body.

Alternatively or additionally, the medical device may further include a motor adapted to rotate the elongate member relative to the suturing body.

Alternatively or additionally, the suture may be attached to a tail piece that is temporarily held in place at a second end of the curved shuttle.

Alternatively or additionally, a portion of the curved shuttle may be adapted to form a tie-off element.

Another example may be found in a medical device that is adapted for use with a delivery system having a lumen extending therethrough. The medical device includes a suturing body adapted to be releasably secured relative to a distal end of the delivery system, the suturing body defining a circular track that extends around a periphery of the suturing body, the circular track including an open portion adapted to allow tissue to enter the open portion. A plurality of electromagnets are disposed within the suturing body. A curved shuttle is disposed within the circular track, the curved shuttle including a pointed leading edge and adapted to hold a suture relative to the curved shuttle. A plurality of permanent magnets are disposed within the curved shuttle. Actuating the electromagnets within the suturing body with an alternating polarity causes the curved shuttle to translate within the circular track.

Alternatively or additionally, the plurality of permanent magnets disposed within the curved shuttle may be arranged with alternating polarity.

Alternatively or additionally, the medical device may further include a control mechanism that controls operation of the plurality of electromagnets disposed within the suturing body.

Alternatively or additionally, the control mechanism may include a push button that can be pushed to change a polarity of one or more of the plurality of electromagnets.

Alternatively or additionally, the control mechanism may include a power supply and a controller that is adapted to control operation of the plurality of electromagnets.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
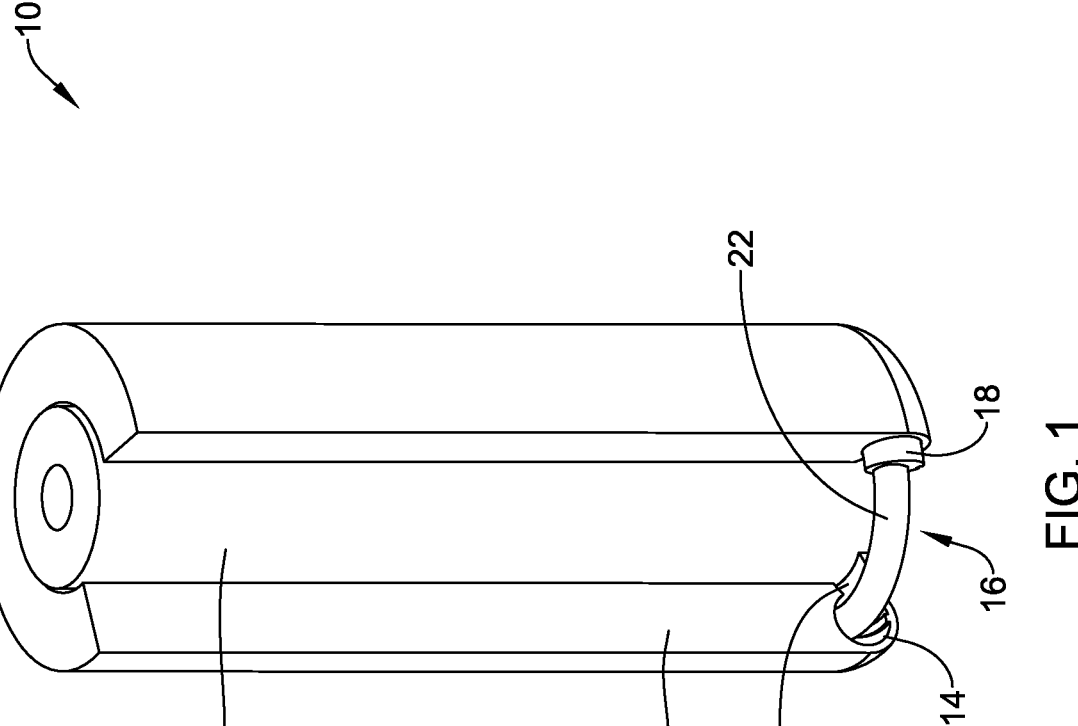
FIG. 1 is a perspective view of an illustrative suture device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some cases may be operated by a single individual, although in some cases a second individual may be involved.

Figures 2A, 2B:
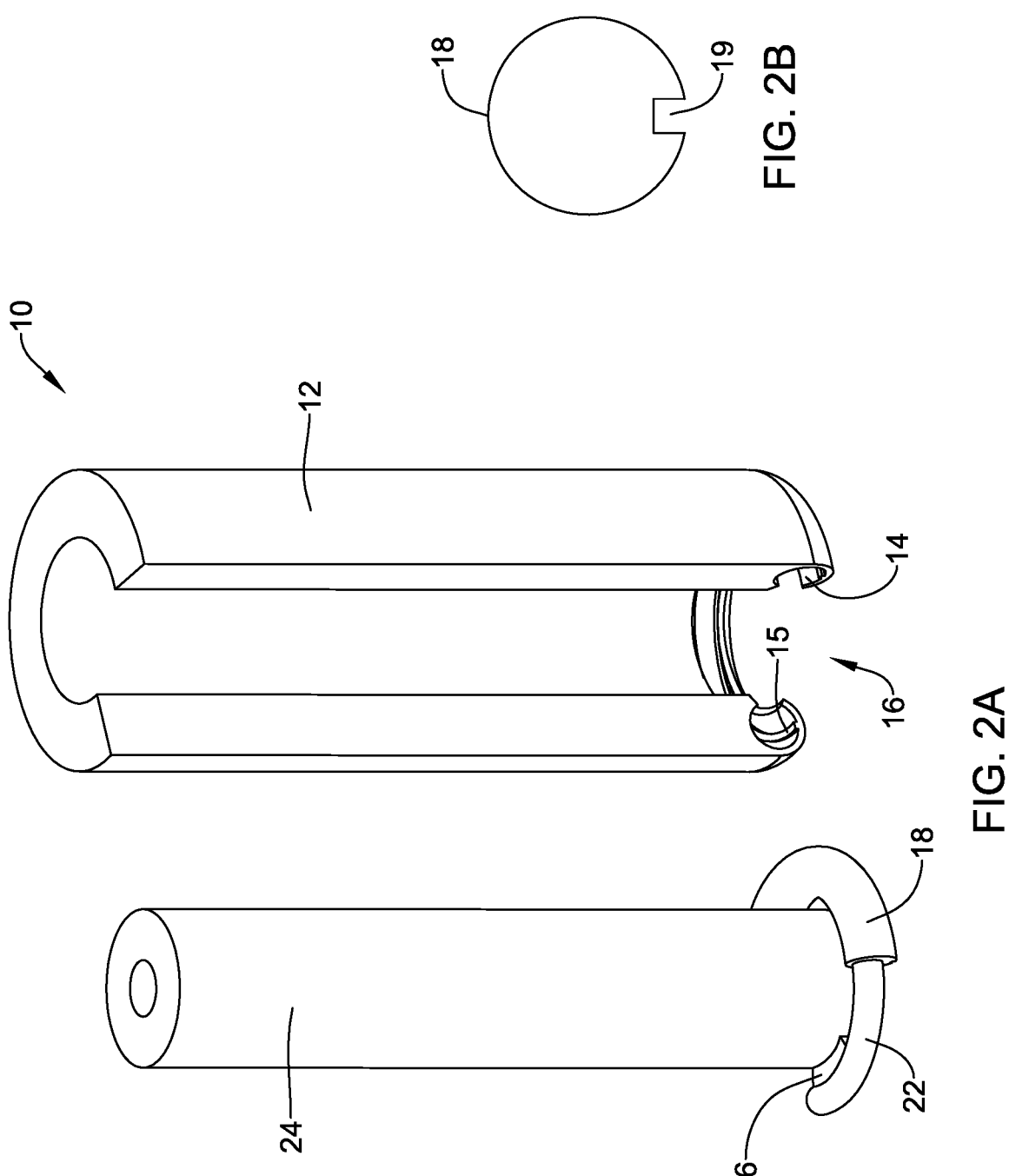
FIG. 2A is an exploded perspective view of the illustrative suture device of FIG. 1.
FIG. 2B is a schematic cross-sectional view of a curved shuttle forming part of the illustrative suture device of FIG. 1.

FIG. 1 is a perspective view and FIG. 2A is an exploded perspective view of an illustrative suture device 10 that may be used in combination with a delivery device including a lumen, such as but not limited to an endoscope having a working channel. The illustrative suture device 10 may be adapted to fit within the working channel of an endoscope, for example. In some cases, the illustrative suture device 10 may be adapted to be secured relative to the distal end of an endoscope or other delivery device. These are just examples.

The suture device 10 includes a suturing body 12 that may be releasably secured relative to a distal end of a delivery system. The suturing body 12 defines a circular track 14 that extends around a periphery of the suturing body 12. In some cases, the circular track 14 has a round cross-sectional profile. In some cases, the elongate body 12 may be considered as being orthogonal to a plane extending through the circular track 14. The circular track 14 includes an open portion 16 that is adapted to allow tissue to enter the open portion 16. The open portion 16 may represent a void equal to about twenty five percent of a total circumference of the circular track 14, for example. Put another way, the open portion 16 may extend about 90 degrees about the suturing body 12 while the circular track 14 extends about 270 degrees about the suturing body 12. In some cases, the open portion 16 may represent a void equal to about five to fifty percent of a total circumference of the circular track 14.

A curved shuttle 18 is disposable within the circular track 14. The curved shuttle 18 has a pointed leading edge 20 (as shown in FIG. 3A) and may be considered as being adapted to hold a suture relative to the curved shuttle 18. As a result, when the curved shuttle 18 is advanced through tissue, a suture is pulled through the tissue by the curved shuttle 18. The curved shuttle 18 may include an aperture that is adapted to hold a suture. In some cases, a suture may be attached to the curved shuttle 18 in any of a variety of different ways. The curved shuttle 18 may be formed of any suitable material, such as but not limited to surgical or stainless steel, cobalt chrome, ferritic steels, Nitinol, and sufficiently rigid polymers such as polycarbonate, PEEK (polyetheretherketone), polyimide and polyurethane. These are just examples.

In some cases, the curved shuttle 18 may have a radius of curvature that substantially equals a radius of curvature of the circular track 14. In this, "substantially equals" means that the radius of curvature of the curved shuttle 18 is close enough to that of the circular track 14 that the curved shuttle 18 is able to easily traverse the circular track 14 without binding. In some cases, the curved shuttle 18 may have a length that is sufficient to ensure that the curved shuttle 18 remains supported by the circular track 14 even while the curved shuttle 18 is traversing the open portion 16. As an example, the curved shuttle 18 may extend about half way around the circular track 14. In some cases, the curved shuttle 18 may be relatively shorter if the open portion 16 is shorter. In some cases, the curved shuttle 18 may be dimensioned relative to the open portion 16 such that the curved shuttle 18 is long enough to be able to span the open portion 16.

In some cases, the suture device 10 includes a curved pusher 22 that is adapted to push the curved shuttle 18 through the circular track 14. In some cases, the curved pusher 22 may be secured relative to an elongate member 24 at an attachment point 26. Accordingly, rotation of the elongate member 24 in an appropriate direction will cause the curved pusher 22 to push the curved shuttle 18 through the circular track 14. In some cases, the elongate member 24 extends proximally from the suture device 10 and may be adapted to be manually rotated. In some cases, as will be discussed, the elongate member 24 may be adapted to be rotated by an electric motor, for example. The curved pusher 22 and the elongate member 24 may be formed of any suitable material, such as but not limited to may be formed of any suitable material, such as but not limited to surgical or stainless steel, cobalt chrome, ferritic steels, Nitinol, and sufficiently rigid polymers such as polycarbonate, PEEK (polyetheretherketone), polyimide and polyurethane. These are just examples.

In some cases, the elongate member 24 may be considered as being coaxial with the suturing body 12. In some cases, the elongate member 24 may extend further proximally than the suturing body 12 does. The suturing body 12 may be shorter, and may be adapted to be secured relative to a delivery device such as an endoscope. In some cases, the suturing body 12 may be long enough to extend proximally through the endoscope. In some cases, a primary function of the suturing body 12 is to define and locate the circular track 14.

In some cases, as indicated in FIG. 2A, the circular track 14 may include a mating raised feature 15 that is a raised portion of the circular track 14. In some cases, as shown in FIG. 2B, the curved shuttle 18 may include a corresponding mating recessed feature 19 that is adapted to engage with the mating raised feature 15. A cooperation between the mating raised feature 15 and the mating recessed feature 19 may help to guide the curved shuttle 18. While the mating raised feature 15 and the corresponding mating recessed feature 19 are both shown as having a square or rectilinear cross-section profile, in some cases, other shapes may be used. For example, the mating raised feature 15 and the corresponding mating recessed feature 19 may each be round or triangular.

While a single mating raised feature 15 and a single mating recessed feature 19 are shown, it will be appreciated that in some cases there may be two, three or more mating raised features 15 distributed circumferentially around the circular track 14 and two, three or more corresponding mating recessed features 19 disposed around the periphery of the curved shuttle 18. In some cases, the circular track 14 may include one or more mating raised features 15 while the curved shuttle 18 does not include any corresponding mating recessed portions 19. In some cases, this may reduce friction between the curved shuttle 18 and the circular track 14.

Figure 3B:
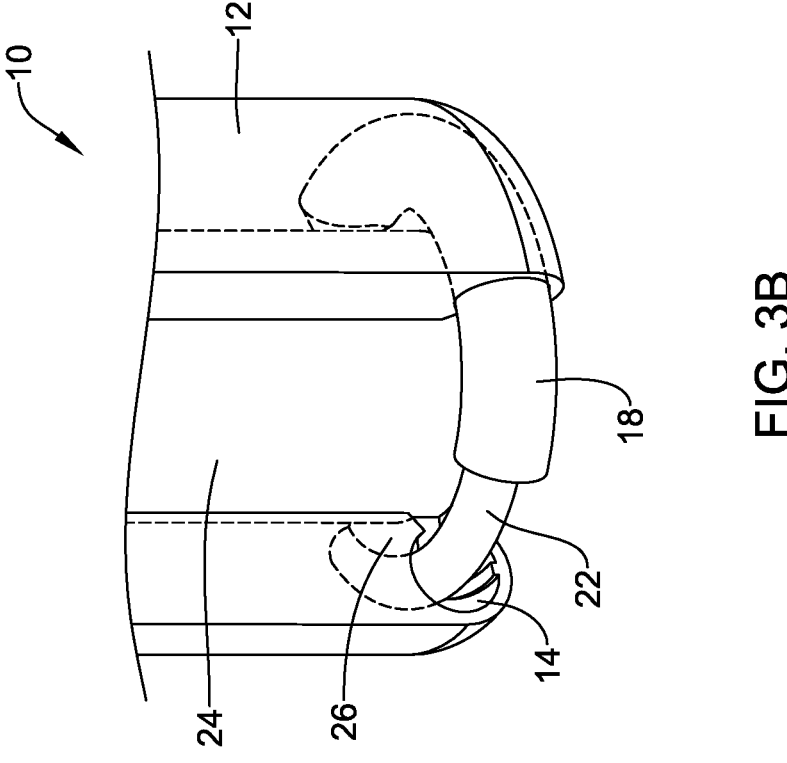
FIGS. 3A, 3B and 3C are schematic views of an illustrative suture device, showing step by step how a suture is mechanically performed.
Figure 3A:
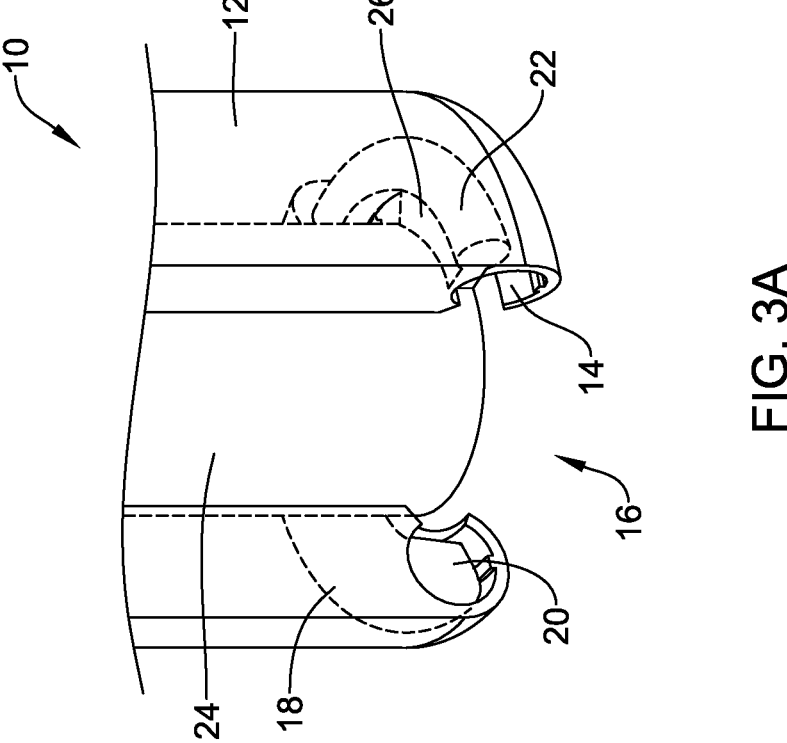
Figure 3C:
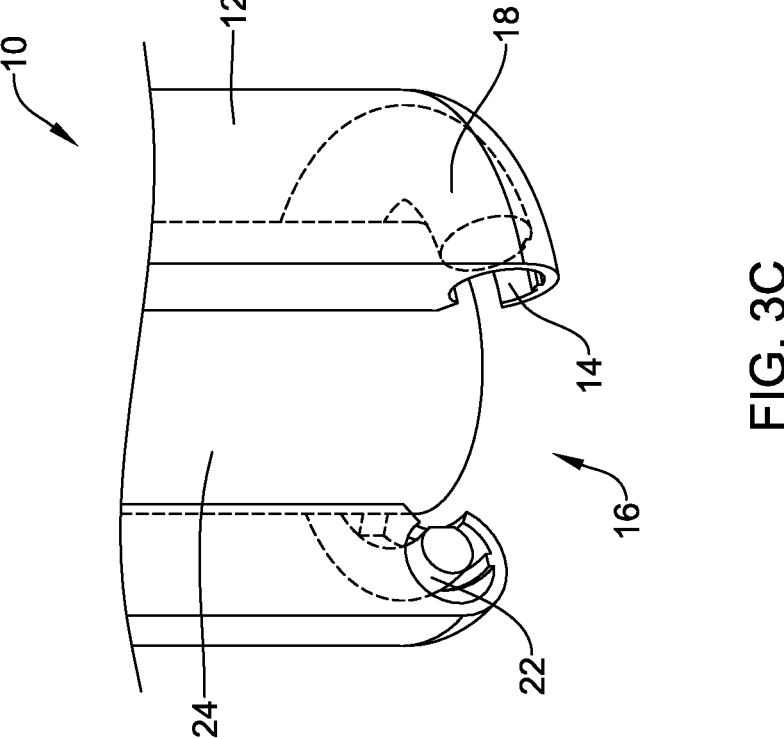

FIGS. 3A, 3B and 3C are schematic views of the illustrative suture device 10, showing step by step how a suture is mechanically performed. FIG. 3A shows the curved shuttle 18 positioned with its pointed leading edge 20 facing the open portion 16. The tissue to be sutured can be urged into position within the open portion 16, such as by using forceps or a coil-like device that could be extended through the center of the device. Next, as shown in FIG. 3B, the curved shuttle 18 is pushed through the open portion 16, and thus through any tissue positioned within the open portion 16. The curved shuttle 18 has been pushed through the open portion 16 by rotating the elongate member 24, which in turn causes the curved pusher 22 to push the curved shuttle 18. Once the curved shuttle 18 has passed completely through the open portion 16, and hence completely through the tissue, the curved pusher 22 may be rotated against the primary direction to remove from the tissue, and the device 10 is moved away from the tissue. This is shown for example in FIG. 3C. Next the elongate member 24 is rotated once again to return to the starting position shown in FIG. 3A.

Figure 4:
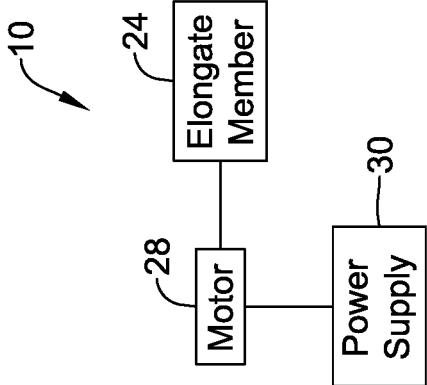
FIG. 4 is a schematic view of an illustrative suture device.

In some cases, as schematically shown in FIG. 4, the suture device 10 may include a motor 28 that is operably coupled with the elongate member 24. As a result, the motor 28 may utilize electrical power from a power supply 30 to rotate the elongate member 24. As the elongate member 24 is rotated, the connection 26 between the curved pusher 22 and the elongate member 24 means that rotation of the motor 28 causes a corresponding rotation of the curved pusher 22 and hence the curved shuttle 18.

Figure 5B:
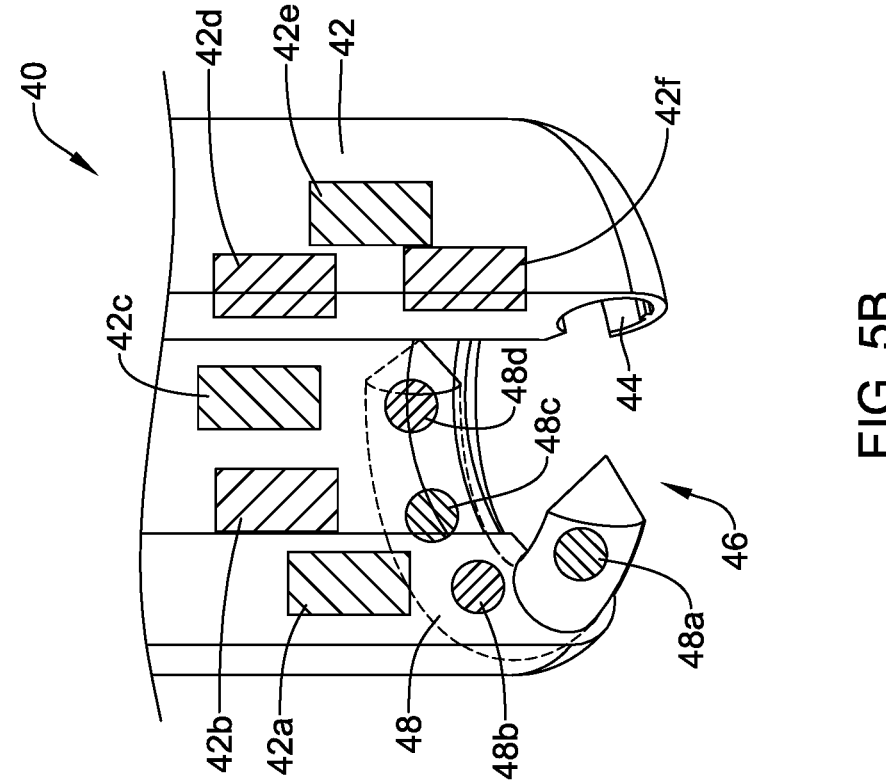
FIGS. 5A, 5B and 5C are schematic views of an illustrative suture device, showing step by step how a suture is electromechanically performed.
Figure 5A:
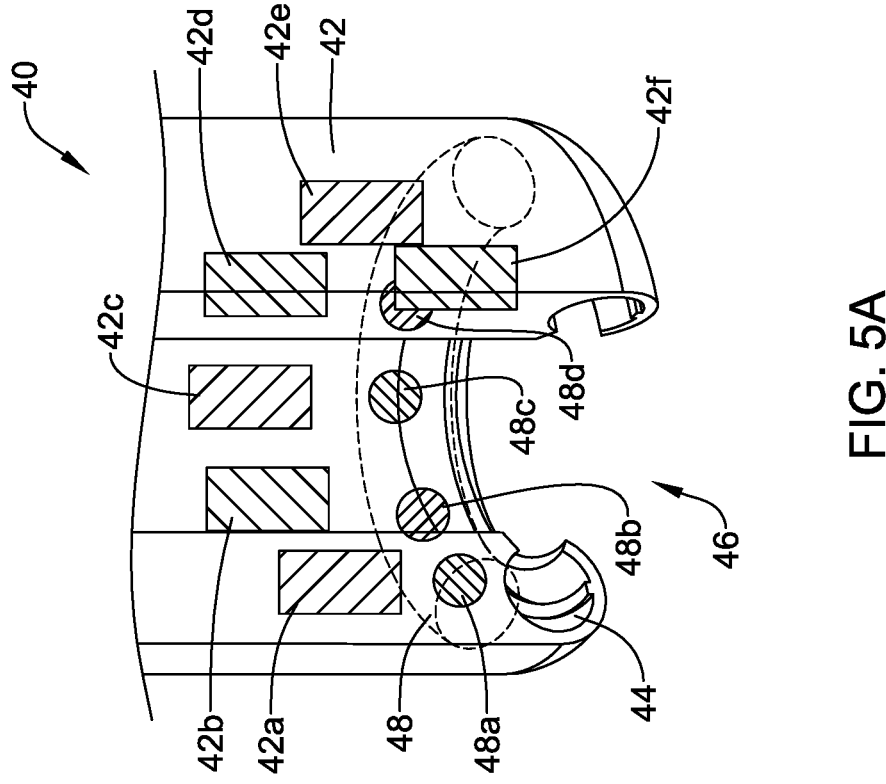
Figure 5C:
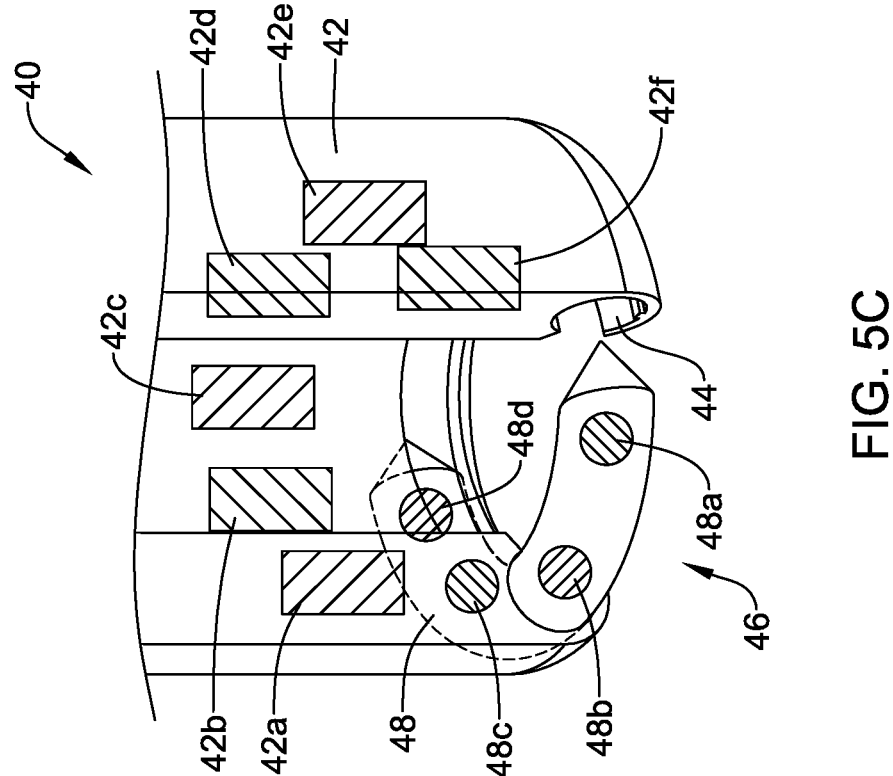

FIGS. 5A, 5B and 5C are schematic views of an illustrative suture device 40, showing step by step how a suture is electromechanically performed. The illustrative suture device 40 includes a suturing body 42 that defines a circular track 44. The circular track 44 includes an open portion 46. A curved shuttle 48 is disposed within the circular track 44. As shown, the curved shuttle 48 includes a permanent magnet 48a, a permanent magnet 48b, a permanent magnet 48c and a permanent magnet 48d. While a total of four permanent magnets are shown, this is merely illustrative, as the curved shuttle 48 may include any number of permanent magnets. In some cases, each of the permanent magnets 48 may have an opposite polarity to that of the neighboring permanent magnets 48. As an example, the permanent magnet 48a may have a first polarity, the second permanent magnet 48b may have a second polarity, the permanent magnet 48c may have the first polarity, and the permanent magnet 48d may have the second polarity.

The suturing body 42 includes a number of electromagnets, including an electromagnet 42a, an electromagnet 42b, an electromagnet 42c, an electromagnet 42d, an electromagnet 42e and an electromagnet 42f. While a total of six electromagnets are shown, this is merely illustrative as the suturing body 42 may include any number of electromagnets. By selecting changing the polarity of each of the electromagnets, it is possible for the resulting magnetic fields to interact with the permanent magnets within the curved shuttle 48 in order to cause the curved shuttle 48 to translate within the circular track 44. In moving from FIG. 5A to 5B, it can be seen that the polarity of the electromagnets has been switched. In moving from FIG. 5B to FIG. 5C, the polarity of the electromagnets has been switched again.

Figure 6:
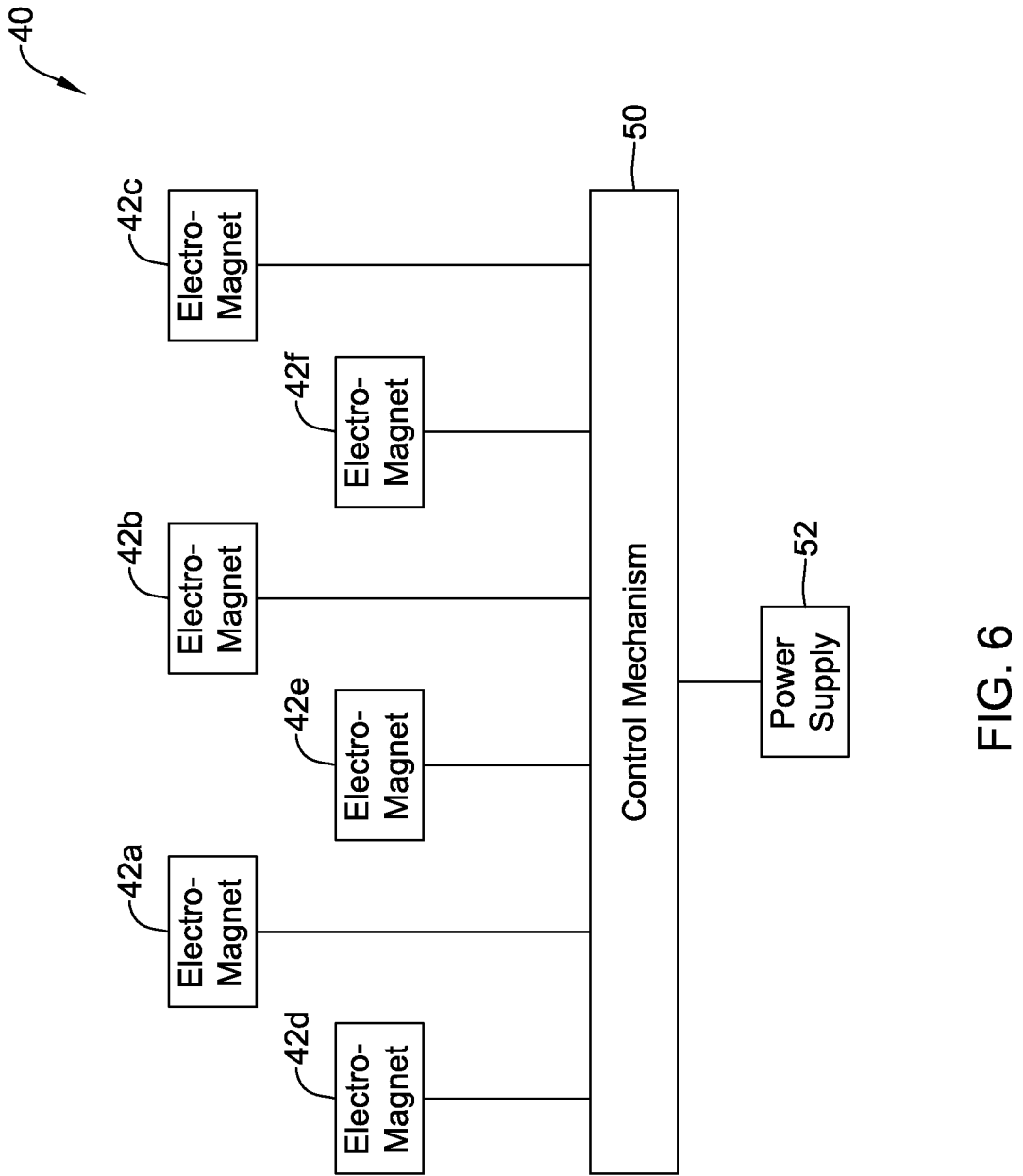
FIG. 6 is a schematic view of an illustrative suture device.

In FIG. 6, the suture device 40 can be seen as including a control mechanism 50 that uses power from a power supply 52 to control operation of each of the electromagnets 42*a*, 42*b*, 42*c*, 42*d*, 42*e* and 42*f* within the suturing body 42. In some cases, the control mechanism 50 may simply include one or more switches, that can be opened or closed to actuate one of the electromagnets 42*a*, 42*b*, 42*c*, 42*d*, 42*e* and 42*f*, or to change a polarity of one or more of the electromagnets 42*a*, 42*b*, 42*c*, 42*d*, 42*e* and 42*f*. In some cases, the control mechanism 50 may include a controller that is programmed to control the polarity of each of the electromagnets 42*a*, 42*b*, 42*c*, 42*d*, 42*c* and 42*f* in order to control the position of the curved shuttle 48.

Figure 7:
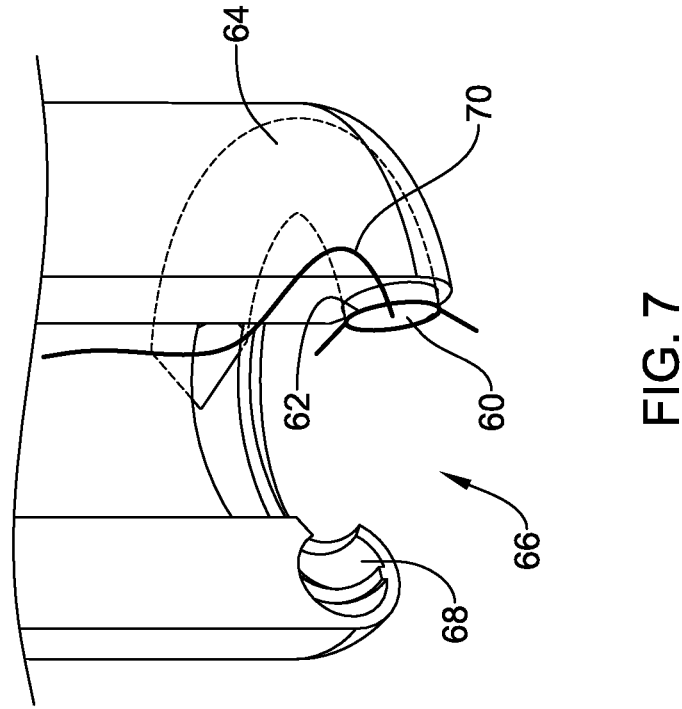
FIG. 7 is a schematic view of an illustrative tail piece providing a suture tie-off.

FIG. 7 is a schematic view of an illustrative tie-off element 60. The illustrative tic-off element 60 is shown temporarily secured relative to a trailing edge 62 of a curved shuttle 64. In some cases, the tie-off element 60 may remain in position until the trailing edge 62 of the curved shuttle 64 passes through an open portion 66 of a circular track 68. As the trailing edge 62 of the curved shuttle 64 passes through the open portion 66, the tie-off element 60 may fall off and become loose. Because a suture 70 extends from the tie-off element 60, the tic-off element 60 may help to initially anchor the suture 70 in position relative to the tissue.

Figure 8:
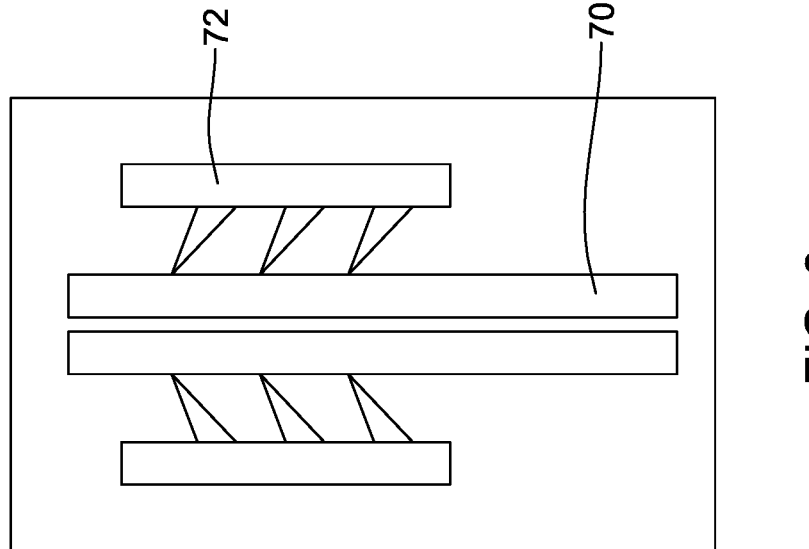
FIG. 8 is a schematic view of a barbed tie-off.

FIG. 8 is a schematic view of an illustrative barbed tie-off element 72 that may be put into position relative to the suture 70 in order to secure a final suture or stitch. In some cases, the tie-off element 72 may also be used to secure the first stitch and to tighten the suture after the last stitch has been secured. In some cases, the barbed tie-off element 72 may be positioned relative to the suture 70 using a tool such as a cannula or a forceps or graspers that is separate from the suture device 10 and/or the suture device 40 described herein. In some cases, the barbed tie-off element 72 may be positioned after the suture device 10 and/or the suture device 40 has been removed.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A suture device adapted for use with an elongate member, the suture device comprising:
   a suturing body adapted to be releasably secured relative to a distal end of the elongate member, the suturing body defining a circular track that extends around a periphery of the suturing body, the circular track including an open portion adapted to allow tissue to enter the open portion;
   a curved shuttle disposed within the circular track, the curved shuttle including a pointed leading edge and adapted to hold a suture relative to the curved shuttle; and
   a curved pusher disposed within the circular track and adapted to push the curved shuttle around the circular track in a first direction around the circular track such that the pointed leading edge penetrates any tissue disposed within the open portion;
   wherein the curved pusher is operably coupleable with the elongate member such that rotation of the elongate member causes the curved pusher to push the curved shuttle around the circular track in the first direction.

2. The suture device of claim 1, wherein the circular track extends within a plane, and the suturing body extends orthogonally to the plane.

3. The suture device of claim 1, wherein the elongate member is adapted to be manually rotated relative to the suturing body.

4. The suture device of claim 1, further comprising a motor adapted to rotate the elongate member relative to the suturing body.

5. The suture device of claim 1, further comprising:
   a plurality of electromagnets disposed within the suturing body; and
   a plurality of magnets disposed within the curved shuttle;
   wherein actuating the electromagnets within the suturing body with an alternating polarity causes the curved shuttle to translate within the circular track.

6. The suture device of claim 1, wherein the suture is attached to a tail piece that is temporarily held in place at a second end of the curved shuttle.

7. A medical device adapted for use with a delivery system having a lumen extending therethrough, the medical device comprising:
   a suturing body adapted to be releasably secured relative to a distal end of the delivery system, the suturing body defining a circular track that extends around a periphery of the suturing body, the circular track including an open portion adapted to allow tissue to enter the open portion;

a curved shuttle disposed within the circular track, the curved shuttle including a pointed leading edge and adapted to hold a suture relative to the curved shuttle;

a curved pusher disposed within the circular track and adapted to push the curved shuttle around the circular track in a first direction around the circular track such that the pointed leading edge penetrates any tissue disposed within the open portion; and an elongate member coupled with the curved pusher such that rotation of the elongate member causes the curved pusher to push the curved shuttle around the circular track in the first direction.

8. The medical device of claim 7, wherein the elongate member extends coaxially through the suturing body.

9. The medical device of claim 8, wherein the elongate member is adapted to be manually rotated relative to the suturing body.

10. The medical device of claim 8, further comprising a motor adapted to rotate the elongate member relative to the suturing body.

11. The medical device of claim 7, wherein the suturing body extends orthogonally to a plane in which the circular track is disposed.

12. The medical device of claim 7, wherein the suture is attached to a tail piece that is temporarily held in place at a second end of the curved shuttle.

13. The medical device of claim 7, wherein a portion of the curved shuttle is adapted to form a tie-off element.

14. A medical device adapted for use with a delivery system having a lumen extending therethrough, the medical device comprising:

a suturing body defining a circular track that extends around a periphery of the suturing body, the circular track including an open portion adapted to allow tissue to enter the open portion;

a shuttle disposed within the circular track;

a pusher disposed within the circular track and configured to push the shuttle around the circular track in a first direction around the circular track to push the suture into contact with the tissue disposed within the open portion; and an elongate member operably coupled with the pusher;

wherein rotation of the elongate member causes the shuttle to translate within the circular track.

15. The medical device of claim 14, further comprising a plurality of permanent magnets disposed within the shuttle and arranged with alternating polarity.

16. The medical device of claim 14, further comprising a control mechanism that controls operation of the plurality of permanent magnets disposed within the suturing body.

17. The medical device of claim 16, wherein the plurality of permanent magnets comprises a plurality of electromagnets and the control mechanism comprises a push button that can be pushed to change a polarity of one or more of the plurality of electromagnets.

18. The medical device of claim 16, wherein the control mechanism comprises:

a power supply; and a controller that is adapted to control operation of the plurality of electromagnets.

\* \* \* \* \*